United States Patent
Fuimaono et al.

(10) Patent No.: US 6,980,858 B2
(45) Date of Patent: Dec. 27, 2005

(54) METHOD AND SYSTEM FOR ATRIAL DEFIBRILLATION

(75) Inventors: Kristine B. Fuimaono, Covina, CA (US); Shahram Moaddeb, Irvine, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 468 days.

(21) Appl. No.: 10/040,977

(22) Filed: Dec. 31, 2001

(65) Prior Publication Data

US 2003/0125770 A1 Jul. 3, 2003

(51) Int. Cl.$^7$ .............................................. A61N 1/365
(52) U.S. Cl. ....................................................... 607/5
(58) Field of Search ................................ 607/5, 6, 122, 607/123, 129, 128; 600/374, 375, 518, 522

(56) References Cited

U.S. PATENT DOCUMENTS

| | | | |
|---|---|---|---|
| 5,010,894 A | 4/1991 | Edhag | |
| 5,165,403 A | 11/1992 | Mehra | |
| 5,391,200 A | 2/1995 | KenKnight et al. | |
| 5,397,341 A | 3/1995 | Hirschberg et al. | |
| 5,423,864 A | 6/1995 | Ljungstroem | |
| 5,449,381 A * | 9/1995 | Imran | 607/122 |
| 5,531,779 A | 7/1996 | Dahl et al. | |
| 5,628,313 A | 5/1997 | Webster, Jr. | |
| 5,855,592 A | 1/1999 | McGee et al. | |
| 5,928,269 A | 7/1999 | Alt | |
| 6,101,410 A | 8/2000 | Panescu et al. | |

OTHER PUBLICATIONS

European Search Report dated Oct. 24, 2003 from corresponding European Application No. EP02259007.9.

* cited by examiner

Primary Examiner—George Manuel
(74) Attorney, Agent, or Firm—Christie, Parker & Hale, LLP

(57) ABSTRACT

A method and system for atrial defibrillation in a patient are provided. The method comprises introducing into the patient a catheter comprising an elongated catheter body having proximal and distal ends and at least one lumen therethrough, and a basket-shaped electrode assembly at the distal end of the catheter body. The electrode assembly has proximal and distal ends and comprises a plurality of spines connected at their proximal and distal ends, each spine comprising an elongated spine electrode along its length. The electrode assembly has an expanded arrangement wherein the spines bow radially outwardly and a collapsed arrangement wherein the spines are arranged generally along the axis of the catheter body. The method further comprises introducing the electrode assembly into the heart of the patient and applying defibrillation energy to the tissue through one or more of the elongated electrodes. The system comprises a catheter as described above in combination with an external defibrillator electrically connected to the catheter.

15 Claims, 6 Drawing Sheets

METHOD AND SYSTEM FOR ATRIAL DEFIBRILLATION

BACKGROUND OF THE INVENTION

Atrial fibrillation (also called "AF" or "A Fib") is the most common abnormal heart rhythm. It is a very fast, uncontrolled heart rhythm caused when the upper changes of the heart (the atria) quiver instead of beating. During atrial fibrillation, the upper chambers of the heart beat between 350 and 600 times per minute, causing the pumping function of the upper chambers to not work properly. As a result, blood is not completely emptied from the heart's chambers, causing it to pool and sometimes clot. In about 5 percent of patients with atrial fibrillation, clotted blood dislodges from the atria and results in a stroke. The American Heart Association estimates that, in the United States, atrial fibrillation is responsible for over 70,000 strokes each year.

Various methods exist for treating atrial fibrillation. One such method is cardiac ablation, which is a medical procedure performed to prevent abnormal electrical impulses from ever beginning in the first place. In an ablation procedure, the electrophysiologist first pinpoints the precise area in the heart at which the abnormal signals start through a mapping procedure. The electrophysiologist then eliminates the small area of tissue that is causing the arrhythmia by ablating that tissue. With a procedure known as AV nodal ablation, the electrophysiologist ablates the AV node, keeping the abnormal impulses from traveling to the heart's lower chambers. A pacemaker is used to regulate the heartbeat after this therapy.

Another method for treating atrial fibrillation is AF suppression. With this method, an implanted pacemaker stimulates the heart in a way that preempts any irregular rhythms.

In about half of the atrial fibrillation cases, medication can be effective in controlling the rate at which the upper and lower chambers of the heart beat. Standard medications used for atrial fibrillation include beta-blockers (such as carvedilol and propanolol) and calcium-channel clockers (like verapamil and diltiazem), which slow the heart rate. Digoxin, which slows the heart rate through the AV node, thereby decreasing the rate at which the electrical impulses conduct from the upper to lower chambers, can also be used. Other medications, such as disopyramide, flecainide, procainamide and sotalol, are used to chemically convert AF back to normal rhythm. In many cases, anticoagulants, such as heparin, are also used to "thin" the blood to reduce the risk of clot formation.

Cardioversion can also be used to treat atrial fibrillation. Cardioversion involves changing an abnormal heart rate back to a normal one. Cardioversion can be done using medication or electricity. In electrical cardioversion, energy is applied to the heart to "jolt" it out of atrial fibrillation. Two types of electrical cardioversion exist, external and internal. For external cardioversion, two external paddles are placed on the patient's chest or on the chest and back. A high-energy electrical shock is sent through the patches and through the body to the heart. The energy shocks the heart out of atrial fibrillation and back into normal rhythm.

Internal cardioversion uses a similar approach, but instead of paddles being placed on the outside of the body, a catheter is inserted through a vein to the heart. The electrical energy is delivered through the catheter to the inside of the heart to stop the atrial fibrillation. Internal cardioversion has met with high success and provides a desirable alternative to external cardioversion. Notably, internal cardioversion requires far lower energy levels than external cardioversion and thus can provide a more comfortable procedure for patients by eliminating the trauma, discomfort and risk associated with high-energy external cardioversion.

Electrophysiologists are developing clinical techniques targeted toward the use of catheter-based ablation as a therapeutic alternative in the treatment of focally induced atrial fibrillation. An important component of these efforts are methods for quickly and reliably inducing and converting the AF arrhythmia while the patient is in the electrophysiology lab.

SUMMARY OF THE INVENTION

The present invention is directed to an method and system for performing internal cardioversion utilizing a catheter having a basket-shaped electrode assembly.

In one embodiment, the invention is directed to a method for atrial defibrillation in a patient in need thereof comprising introducing into the patient a catheter. The catheter comprises an elongated catheter body having proximal and distal ends and at least one lumen therethrough, and a basket-shaped electrode assembly at the distal end of the catheter body. The electrode assembly has proximal and distal ends and comprises a plurality of spines connected at their proximal and distal ends, each spine comprising an elongated spine electrode along its length. The electrode assembly has an expanded arrangement wherein the spines bow radially outwardly and a collapsed arrangement wherein the spines are arranged generally along the axis of the catheter body. The method further comprises introducing the electrode assembly into the heart of the patient and applying defibrillation energy to the tissue through one or more of the elongated electrodes.

In another embodiment, the invention is directed to a system for atrial defibrillation in a patient. The system comprises a catheter as described above in combination with an external defibrillator electrically connected to the catheter.

In a particularly preferred embodiment, the invention is directed to a system for atrial defibrillation in a patient comprising a catheter. The catheter comprises an elongated catheter body having proximal and distal ends, a length of at least about 90 cm, and at least one lumen therethrough. The catheter body has one or more ring electrodes mounted at or near its distal end. The catheter further comprises a basket-shaped electrode assembly at the distal end of the catheter body, the electrode assembly having proximal and distal ends and comprising at least three spines connected at their proximal and distal ends. Each spine comprises an elongated spine electrode along its length, wherein each spine electrode has a length ranging from about 30 mm to about 80 mm. The electrode assembly has an expanded arrangement wherein the spines bow radially outwardly and a collapsed arrangement wherein the spines are arranged generally along the axis of the catheter body. The electrode assembly has a tip electrode mounted at its distal end. The system further comprises an external defibrillator electrically connected to the catheter, an interface switch box that connects the external defibrillator to the catheter and that permits the selection of spine electrodes through which defibrillation energy is to be delivered, an ECG recorder electrically connected to the catheter through the interface switch box, and an external pacer electrically connected to the catheter through the interface switch box.

The inventive method and system offer several advantages over existing methods and systems. First, the basket-shaped electrode assembly has a larger surface area than conventional catheters and permits better current distribution to cover a majority of both atria during treatment. The larger surface area also reduces the impedance and energy requirements. The ability of the electrode assembly to expand and contract permits adjustability of the electrodes and better contact with tissue. The electrode assembly can also be placed within the pulmonary artery for better current distribution in the left atrium.

DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
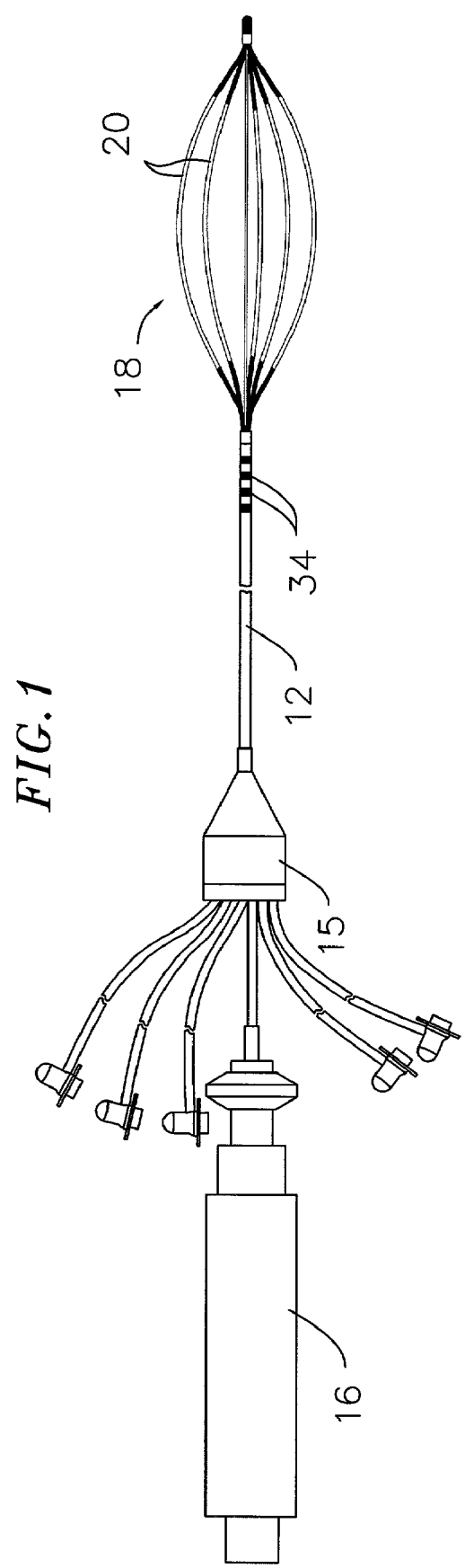
FIG. 1 is a perspective view of a catheter according to the invention.

The invention is directed to a method and system for atrial defibrillation using a catheter having a basket-shaped electrode array at its distal end. As shown in FIG. 1, the catheter 10 comprises an elongated catheter body 12 having proximal and distal ends, a connector 15 and a control handle 16 at the proximal end of the catheter body, and a basket-shaped electrode assembly 18 mounted at the distal end of the catheter body 12.

In accordance with the invention, the catheter body 12 comprises an elongated tubular construction having a single, axial or central lumen (not shown), but can optionally have multiple lumens if desired. The catheter body 12 is flexible, i.e., bendable, but substantially non-compressible along its length. The catheter body 12 can be of any suitable construction and made of any suitable material. A presently preferred construction comprises an outer wall made of polyurethane or PEBAX® (polyether block amide). The outer wall comprises an imbedded braided mesh of stainless steel or the like to increase torsional stiffness of the catheter body 12 so that, when the control handle 16 is rotated, the distal end of the catheter body will rotate in a corresponding manner.

The length of the catheter, i.e, the catheter body 12 and mapping assembly 18 excluding the connector 15 and control handle 16, is preferably at least about 90 cm, more preferably from about 110 cm to about 120 cm, still more preferably about 115 cm. The outer diameter of the catheter body 12 is not critical, but is preferably no more than about 8 french, more preferably 7 french. Likewise the thickness of the outer wall is not critical, but is preferably thin enough so that the central lumen can accommodate a puller wire, lead wires, sensor cables and any other wires, cables or tubes. An example of a catheter body construction suitable for use in connection with the present invention is described and depicted in U.S. Pat. No. 6,064,905, the entire disclosure of which is incorporated herein by reference.

Figure 2:
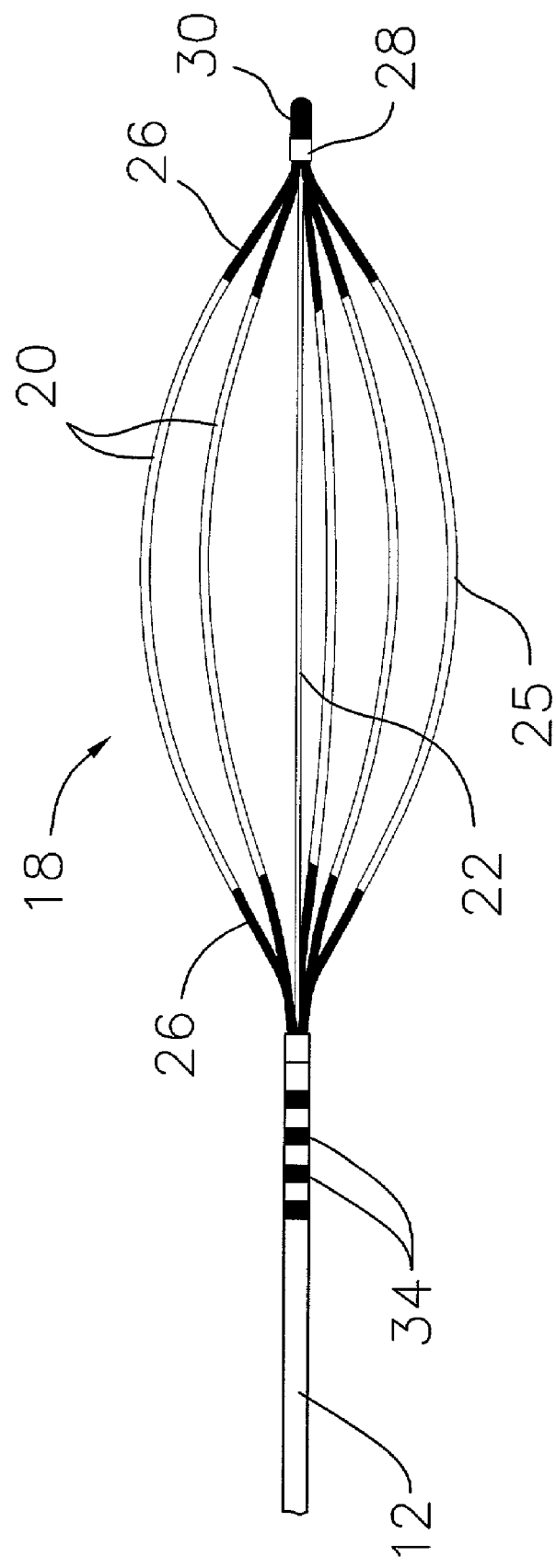
FIG. 2 is a close-up perspective view of the basket-shaped electrode assembly and the distal end of the catheter body of the catheter shown in FIG. 1.

The basket-shaped electrode assembly 18 is mounted to the distal end of the catheter body 12. As shown in FIGS. 1 and 2, the basket-shaped electrode assembly 18 comprises five spines 20 or arms. The spines 20 are all attached, directly or indirectly, to each other at their proximal and distal ends, and to the catheter body 12 at their proximal ends. The basket-shaped electrode assembly 18 is moveable between an expanded position and a contracted position, so that, in the expanded position the spines 20 are bowed outwardly and in the contracted position the spines are generally straight and arranged generally along the axis of the catheter body. As will be recognized by one skilled in the art, the number of spines 20 can vary as desired depending on the particular application, so that the assembly has at least two spines, preferably at least three spines, more preferably at least five spines, and as many as eight or more spines.

Expansion and contraction of the electrode assembly 18 can be accomplished by any suitable means. For example, as shown in FIG. 2, the assembly 18 includes an expander 22 attached at its distal end to the distal ends of the spines 20 with the spines mounted, preferably generally evenly-spaced, around the expander so that the expander forms the axis of the electrode assembly. The expander 22 is generally coaxial with the catheter body 12. The expander 22 extends through the catheter body and out the proximal end of the catheter body, preferably into a suitable control handle 16, as discussed further below. The expander 22 is not connected to the catheter body 12, so that longitudinal movement of the expander relative to the catheter body results in expansion and contraction of the electrode assembly 18.

The expander 22 can comprise a wire, such as a Nitinol wire, that optionally extends through a non-conductive tubing (not shown) outside of the catheter body 12. Alternatively, the expander 22 can comprise a flexible tubing having a lumen (not shown) extending through its entire length. The lumen permits a guidewire to extend through the entire length of the catheter for introduction of the catheter into the body and so that the electrode assembly 18 can be removed and later reintroduced to the same position, if desired. In a preferred embodiment, the expander 22 comprises braided polyimide tubing, i.e., tubing having inner and outer layers of polyimide with a braided stainless steel mesh therebetween, as is generally known in the art. A more detailed description of a catheter having a basket-shaped electrode assembly with such an expander is disclosed in copending application entitled "BASKET CATHETER WITH MULTIPLE LOCATION SENSORS," filed on Dec. 14, 2001, the disclosure of which is incorporated herein by reference.

Each spine 20 comprises a flexible wire 24 that forms an elongated spine electrode 25 along at least a portion of its length. The elongated electrode 25 preferably has a length ranging from about 10 mm to about 100 mm, more preferably from about 30 mm to about 80 mm, still more preferably from about 50 to about 60 mm. In a preferred embodiment, the flexible wires 24 each comprise a flat or round Nitinol wire. The flexible wires 24 are insulated from one another at their proximal and distal ends. In the depicted embodiment, each wire 24 has non-conductive coverings 26 at its proximal and distal ends, with the remainder being exposed to form the spine electrode 25. As would be recognized by one skilled in the art, the elongated spine electrodes 25 could have other suitable designs such that the are of sufficient length. For example, the flexible wires 24 could be covered along their entire length with a non-conductive covering 26, with an elongated electrode then placed over the non-conductive covering.

In a preferred embodiment, the distal ends of the spines 20 are connected and covered by a plastic, preferably polyurethane, cap 28. If desired, the distal ends of the spines 20 can be held in place within the cap 28 using polyurethane glue or the like. A tip electrode 30 is mounted on the distal end of the plastic cap 28, preferably for use as a pacing electrode, as discussed in more detail below. Alternatively, the tip electrode 30 can be used as a mapping electrode. The tip electrode 30 can comprise any suitable conductive metal, such as gold or platinum, and preferably an alloy of platinum and iridium.

Each of the spine electrodes 25 and tip electrode 30 is electrically connected to a suitable source of energy, as discussed further below, by an electrode lead wire 32. An electrode lead wire 32 can be attached to the spine electrodes 25 and tip electrode 30 by any suitable means, preferably by solder of the like. Each electrode lead wire 32 attached to a spine electrode 25 is attached to the proximal end of the corresponding electrode, extends through a lumen in the catheter body 12 and is attached to the connector 17. The lead wire 32 for the tip electrode 30 is attached to the tip electrode 30, extends through a lumen in the expander 22, extends through the catheter body 12, and is attached at its proximal end to the connector 17. Each lead wire 32 is attached to its corresponding spine electrode 25 or tip electrode 30 by any suitable method, preferably solder or the like.

In the depicted embodiment, four ring electrodes 34 are mounted along the distal end of the catheter body 12. Each ring electrode 34 preferably comprises a ring of platinum, gold or a combination of platinum and iridium. The ring electrodes 34 can be used for pacing, for detecting electrical signals before, during or after defibrillation [please confirm], or for a return electrode for defibrillation, as discussed further below. As would be recognized by one skilled in the art, the presence and number of ring electrodes 34 can vary depending on the particular application.

An electrode lead wire 32 is attached to each ring electrode 34 by any suitable method. A preferred method for attaching a lead wire 32 to a ring electrode 34 involves first making a small hole through the outer wall of the catheter body 12. Such a hole can be created, for example, by inserting a needle through the wall of the catheter body 12 and heating the needle sufficiently to form a permanent hole. The lead wire 32 is then drawn through the hole by using a microhook or the like. The end of the lead wire 32 is then stripped of any coating and welded to the underside of the ring electrode 34, which is then slid into position over the hole and fixed in place with polyurethane glue or the like. Alternatively, each ring electrode 34 may be formed by wrapping the lead wire 32 around the catheter body 12 a number of times and stripping the lead wire of its own non-conductive coating on its outwardly facing surfaces.

Figure 3:
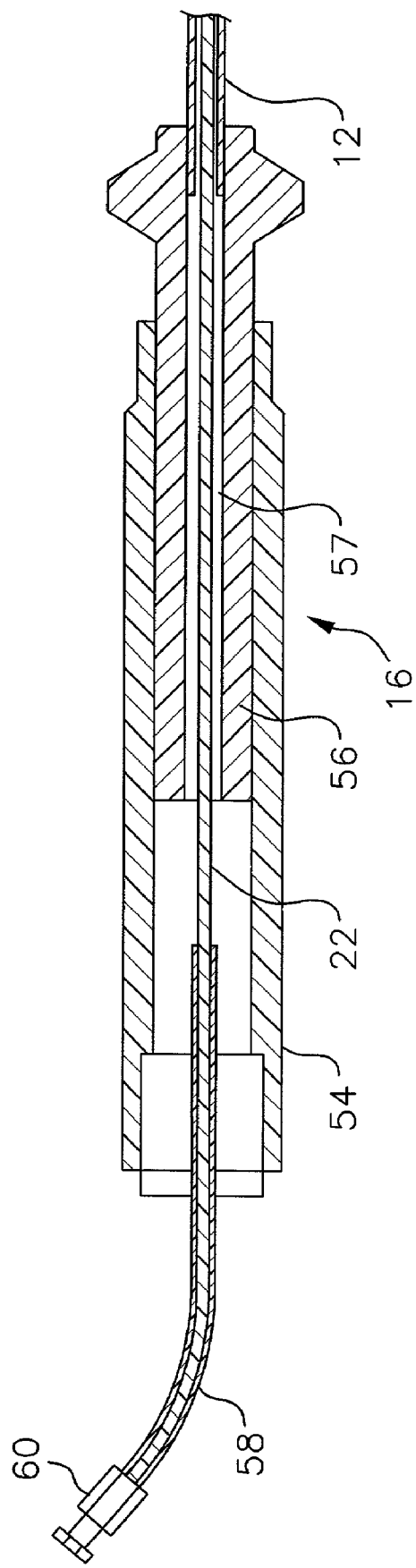
FIG. 3 is a side cross-sectional view of the control handle of the catheter shown in FIG. 1

Longitudinal movement of the expander 22 relative to the catheter body 12, which results in expansion of the electrode assembly 18, is accomplished by manipulation of the control handle 16. As shown in FIG. 3, the control handle 16 comprises a generally-hollow handle housing 54 and a piston 56 slidably mounted within the distal end of the handle housing. The proximal end of the catheter body 12 is fixedly attached to the distal end of the piston 56 by a shrink sleeve (not shown), as is generally known in the art, or by any other suitable method.

Within the control handle 16, the proximal end of the expander 22 extends through a passage 57 in the piston 56, through the handle housing 54 and into a support tube 58, preferably made of braided polyimide or PEBAX®. The support tube 58 extends out the proximal end of the control handle 16 and terminates in a luer hub 60. The support tube 58 and expander 22 are together fixedly attached to the handle housing 54 by any suitable method, preferably with polyurethane glue or the like. If the expander 22 does not have a lumen, e.g., is in the form of a puller wire or the like, the expander can be attached to the handle housing 54 without the use of the support tube 58 and luer hub 60, as is generally known for handles for steerable catheters. Examples of such handle designs are disclosed in U.S. Pat. Nos. Re 34,502 and 5,897,529, the disclosures of which are incorporated herein by reference.

Figure 4:
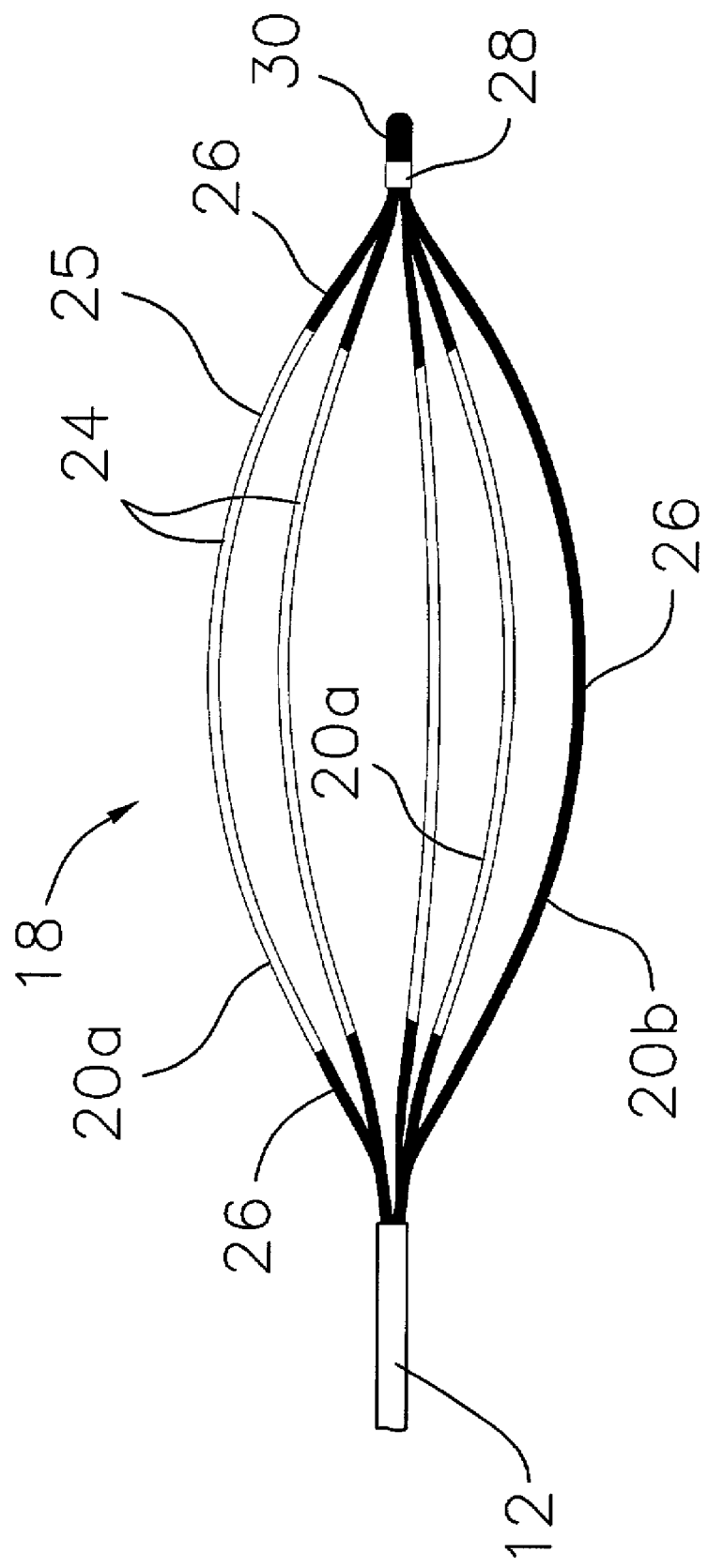
FIG. 4 is a perspective view of an alternative basket-shaped electrode assembly in accordance with the invention.

If desired, the expander can be eliminated. With such a design, the basket-shaped mapping assembly 18 may be expanded and contracted by moving a guiding sheath proximally off the basket and distally over the basket, respectively, so that the catheter itself does not need to include a means for expanding and contracting the basket. In this embodiment, as shown in FIG. 4, the mapping assembly 18 include five spines, but only four of the spines 20a form electrodes 25. The fifth spine 20b comprises a flexible wire 24 having a non-conductive covering 26 over its entire length. The electrode lead wire 32 for the tip electrode extends along the fifth spine 20b within the non-conductive covering 26 and then into the catheter body 12, as generally described above with respect to the embodiment shown in FIG. 2.

If desired, the catheter can include one or more location sensors (not shown) for providing location information about the electrode assembly 18. Such a design is particularly useful if the an electrical map of the heart has been produced by a mapping catheter having one or more location sensors. The electrophysiologist can then use the location sensors to determine the proper placement of the electrode assembly 18. A catheter having a basket-shaped electrode assembly with location sensors is described in copending application entitled "BASKET CATHETER WITH MULTIPLE LOCATION SENSORS," filed on Dec. 14, 2001.

Figure 5:
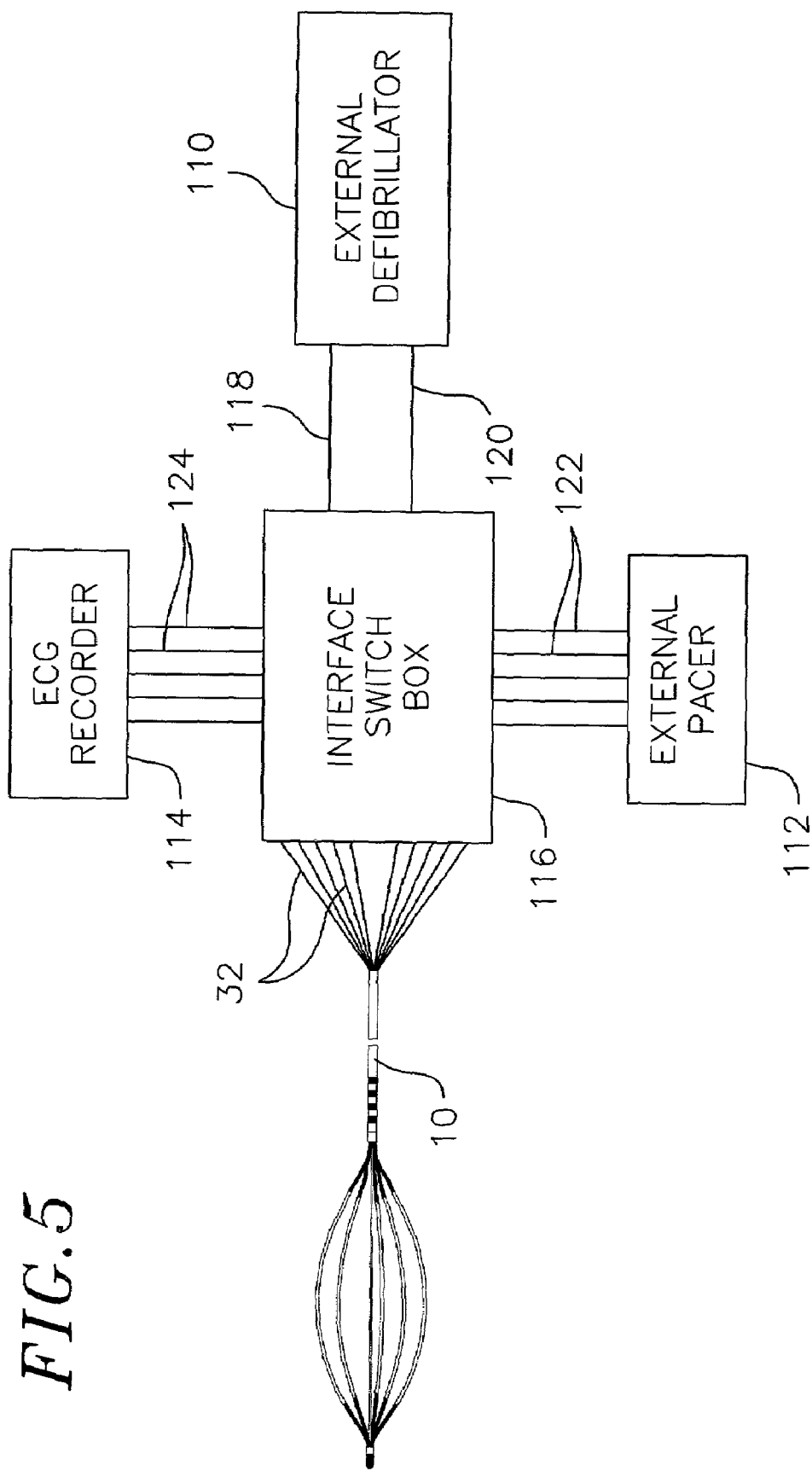
FIG. 5 is a schematic diagram of a system in accordance with the invention.

As shown generally in FIG. 5, the catheter of the invention is used in connection with a suitable external defibrillator 110, an external pacer 112, and an ECG recorder 114, which are all connected via an interface switch box 116. Any suitable external defibrillator, external pacer and ECG recorder known in the art can be used in connection with the invention. The interface switch box 116 provides a centralized connection to the other system components while also facilitating electrode selection.

Specifically, cardioversion can be achieved using various electrode arrangements. For example, cardioversion can be achieved internally by shorting together all of the spine electrodes 25 so that they can together be used as a single shocking electrode. Shorting of the spine electrodes 25 is achieved using the interface switch box, as is generally known in the art. In such an embodiment, one or more of the ring electrodes 34 on the catheter body 12 and/or the tip electrode 30 mounted on the electrode assembly 18 can be used as the return electrode, and preferably multiple ring electrodes are shorted together to form a return electrode. With this embodiment, a large shocking electrode surface is formed with the five spine electrodes 25.

Cardioversion can also be achieved internally by using less than all of the spine electrodes 25 as a shocking electrode and using the remaining spine electrodes as a return electrode. For example, with the embodiment shown in FIG. 4, two of the spine electrodes 25 can be shorted together to form a shocking electrode, with the two remaining spine electrodes shorted together to form the return electrode. In this embodiment, a relatively large shocking electrode surface is formed using two spine electrodes.

Alternatively, cardioversion can be achieved with a combination of internal and external electrodes. For example, one or more of the spine electrodes 25 can be used as the shocking electrode, as generally described above. An electrode patch (not shown) is provided on the outside of the patient's body and electrically connected to the external defibrillator 110 through the interface switch box 116. The electrode patch serves as the return electrode for defibrillation.

As shown in FIG. 5, the external defibrillator 110 has two electrical connections to the interface switch box 116, namely, a shocking connection 118 through which electrical energy to the one or more shocking electrodes is delivered, and a return connection 120 through which electrical energy passes to the defibrillator from the return electrodes. The defibrillator delivers sufficient energy to achieve defibrillation, preferably from about 0.5 to about 20 joules, more preferably from about 1 to about 10 joules, still more preferably from about 1 to 4 joules. The energy is preferably delivered over a period of time ranging from about 2 to about 10 msec, more preferably about 6 msec. The shape of the energy delivered can be uniphasic, biphasic, or multiphasic.

The external pacer 112 is electrically connected to the interface switch box 116 by one or more pacer connections 122 depending on the number of pacing electrodes on the catheter. In the depicted embodiment, the catheter includes one tip electrode 30 and four ring electrodes 34 that can be use for pacing, and thus the system includes five pacer connections 122.

The ECG recorder 114 is similarly connected to the interface switch box 116 by one or more recorder connections 124 depending on the number of electrodes available for obtaining ECG information. In the depicted embodiment, the catheter includes one tip electrode 30 and four ring electrodes 34 that can be used for obtaining electrical information, and thus the system includes five recording connections 124.

To use the catheter of the invention, an electrophysiologist introduces a guiding sheath, guidewire and dilator into the patient, as is generally known in the art. A suitable guiding sheath for use in connection with the inventive catheter is the PREFACE™ Braided Guiding Sheath (commercially available from Biosense Webster, Inc., Diamond Bar, Calif.). The dilator is removed, and the catheter is introduced through the guiding sheath whereby the guidewire lumen in the expander 22 permits the catheter to pass over the guidewire. The guiding sheath covers the spines 20 of the electrode assembly 18 internally in a collapsed position so that the entire catheter can be passed through a vein or artery to a desired location. Once the distal end of the catheter reaches the desired location, the guiding sheath is withdrawn. The expander 22 is then manipulated so that the spines 20 of the electrode assembly 18 flex outwardly into an expanded arrangement. In such an arrangement the spines 20 (and thus spine electrodes 25) contact the tissue of the heart. As will be recognized by one skilled in the art, the electrode assembly 18 can be fully or partially expanded in a variety of configurations depending on the precise configuration of the region of the heart in which the assembly is positioned.

Once the electrode assembly 18 is in the desired position, the system is set up. The catheter 10 is electrically connected to the interface switch box 116 via the electrode lead wires 32, which can be done before or after insertion of the catheter. The interface switch box 116 is also electrically connected to the external defibrillator 110, external pacer 112, and ECG recorder 114, as described above. The electrode impedance is verified through the external defibrillator 110 and/or external pacer 112. The intercardiac ECG amplitude is also verified to assure that the electrodes are working properly and in good contact with the heart tissue. The electrophysiologist then selects the electrode, defibrillation and pacing modes, as well as the defibrillation parameters (such as energy and pulse width) to be delivered through the external defibrillator.

After the electrode assembly 18 is in the desired position and the system set up, the electrophysiologist can then introduce into the patient's heart a suitable treatment catheter, such as an ablation catheter for ablating lines of block. The electrophysiologist performs the ablation or other atrial fibrillation treatment, as is generally known in the art. It is not uncommon for the patient's heart to stop beating during such procedures. Accordingly, to the extent this occurs, the electrophysiologist uses the basket catheter of the invention to deliver shocking energy to the heart. To do so, the electrophysiologist synchronizes cardioversion with the R-wave and then delivers the defibrillation energy to the heart. The electrophysiologist then verifies capture, and if there is not capture, he redelivers the defibrillation energy.

As noted above, because the basket-shaped electrode assembly has a larger surface area than conventional catheters, the impedance and energy requirements are reduced, thereby causing less pain to the patient than with conventional defibrillation methods. Moreover, the ability of the electrode assembly to expand and contract permits adjustability of the electrodes and better contact with tissue. After the patients achieves a regular heartbeat, the electrophysiologist can resume the ablation or other treatment procedure. Additionally, the basket catheter of the invention can be used for pacing during the ablation or other treatment procedure using the tip electrode and/or ring electrodes.

Although the inventive methods and systems have been described with respect to a particularly preferred basket catheter configuration, other similar basket catheter configurations can also be used. Examples of such configurations are generally described in U.S. Pat. Nos. 6,262,695, 5,782,239, 5,772,590, 5,628,313, and 5,411,025, the disclosures of which are incorporated herein by reference.

Figure 6:
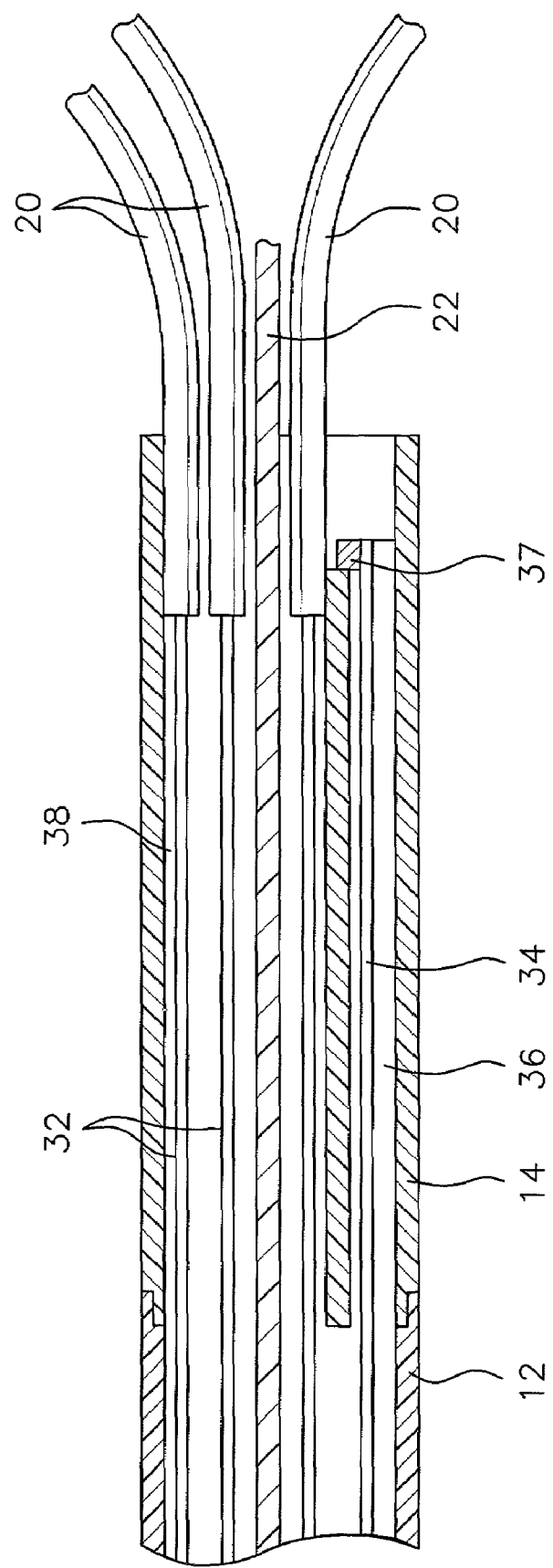
FIG. 6 is a side cross-sectional view of the distal end of a catheter according to the invention showing an exemplary steering mechanism.

If desired, the catheter can include a steering mechanism for deflection of the distal end of the catheter body 12. With such a design, the distal end of the catheter body 12 preferably includes a tip section 14 comprising a short length of tubing, e.g., 2 to 4 inches, that is more flexible than the remainder of the catheter body, as shown in FIG. 6. The tip section 14 can be attached to the catheter body 12 by any suitable method, such as by polyurethane glue or the like, as described in more detail in U.S. patent application Ser. No. 09/796,198, entitled "Catheter Having Continuous Braided Electrode," the entire disclosure of which is incorporated herein by reference.

The steering mechanism comprises a puller wire 34 that extends from a proximal end in the handle through the catheter body and into an off axis lumen 36 in the tip section 14. The tip section 14 comprises a primary lumen 38, which can be an off-axis lumen or an axial lumen, into which the expander 22, electrode lead wires 32 and the proximal ends of the spines 20 extend. Within the catheter body 12, the puller wire preferably extends through a closely wound coil (not shown) that is bendable but substantially compressible, as generally described in U.S. patent application Ser. No.

09/796,198, entitled "Catheter Having Continuous Braided Electrode," the entire disclosure of which is incorporated herein by reference. Preferably the coil is fixed near the proximal and distal ends of the catheter body to prevent deflection of the catheter body. The distal end of the puller wire 34 is anchored in the tip section 14 proximal to the proximal end of the electrode assembly 18 by any suitable means. In the depicted embodiment, the puller wire 34 is anchored to the distal end of the tip section 14 with a T-shaped anchor 37, as generally described in U.S. patent application Ser. No. 09/796,198, entitled "Catheter Having Continuous Braided Electrode," the entire disclosure of which is incorporated herein by reference. As described in U.S. patent application Ser. No. 09/796,198, the T-shaped anchor can also be used to attach the puller wire to the side wall of the tip section.

The proximal end of the puller wire 34 is anchored to a movable member in the control handle 16 that can be moved relative to the catheter body 12. If the catheter does not include an expander 22, the above-described control handle 16 can be used for manipulating the puller wire 34 in place of the expander, as would be recognized by one skilled in the art. In other words, the proximal end of the puller wire 34 is attached, directly or indirectly, to the handle housing 54 so that proximal movement of the handle housing relative to the piston 56 and catheter body 12 results in longitudinal movement of the puller wire 34 relative to the catheter body, thereby deflecting the tip section 14. If a steering mechanism is included in addition to an expander 22, the control handle 16 may be of any suitable construction for manipulating two wires, in this case, the expander 22 and the puller wire 34. Preferably the handle has a pair of movable members to which the expander and puller wire attach, such as handles typically used for bidirectional and multidirectional catheters. Examples of such handles are disclosed in U.S. Pat. Nos. 6,210,407, 6,198,974, 6,183,463, 6,183,435, 6,171,277, and 6,123,699, the disclosures of which are incorporated herein by reference.

The preceding description has been presented with references to presently preferred embodiments of the invention. Persons skilled in the art and technology to which this invention pertains will appreciate that alterations and changes in the described structures and methods can be practiced without meaningfully departing from the principle, spirit and scope of this invention. Accordingly, the foregoing description should not be read as pertaining only to the precise structures and methods described and shown in the accompanying drawings, but rather should be read as consistent with and as support for the following claims, which are to have their fullest and fairest scope.

What is claimed is:

1. A method for atrial defibrillation in a patient in need thereof comprising:
   introducing into the patient a catheter comprising:
      an elongated catheter body having proximal and distal ends and at least one lumen therethrough, and
      a basket-shaped electrode assembly at the distal end of the catheter body, the electrode assembly having proximal and distal ends and comprising a plurality of spines connected at their proximal and distal ends, each spine comprising an elongated spine electrode along its length, the electrode assembly having an expanded arrangement wherein the spines bow radially outwardly and a collapsed arrangement wherein the spines are arranged generally along the axis of the catheter body;
   introducing the electrode assembly into the heart of the patient; and
   applying defibrillation energy to tissue of the heart through one or more of the elongated electrodes, wherein defibrillation energy is delivered to the heart tissue through only a portion of the spine electrodes, leaving one or more spine electrodes through which defibrillation energy is not delivered to the heart tissue, wherein the spine electrodes through which defibrillation energy is delivered are shorted together.

2. The method of claim 1, wherein defibrillation energy is delivered to the heart tissue through at least half of the spine electrodes.

3. The method of claim 1, wherein the one or more spine electrodes through which defibrillation energy is not delivered to the heart tissue are shorted together and function as a return electrode for the defibrillation energy.

4. A system for atrial defibrillation in a patient comprising:
   a catheter comprising:
      an elongated catheter body having proximal and distal ends, a length of about 90 cm, and at least one lumen therethrough, and
      a basket-shaped electrode assembly at the distal end of the catheter body, the electrode assembly having proximal and distal ends and comprising a plurality of spines connected at their proximal and distal ends, each spine comprising an elongated spine electrode along its length, the electrode assembly having an expanded arrangement wherein the spines bow radially outwardly and a collapsed arrangement wherein the spines are arranged generally along the axis of the catheter body;
   an external defibrillator electrically connected to the catheter; and
   an interface switch box that connects the external defibrillator to the catheter and that permits the selection of the spine electrodes through which defibrillation energy is to be delivered.

5. The system of claim 4, further comprising an ECG recorder electrically connected to the catheter through the interface switch box.

6. The system of claim 5, wherein the catheter further comprises one or more ring electrodes mounted at or near the distal end of the catheter body.

7. The system of claim 4, further comprising an external pacer electrically connected to the catheter through the interface switch box.

8. The system of claim 7, wherein the catheter further comprises a tip electrode mounted at the distal end of the electrode assembly.

9. The system of claim 4, wherein each spine comprises a flexible wire having proximal and distal ends, wherein at least a portion of the flexible wire forms the elongated electrode.

10. The system of claim 4, wherein the electrode assembly comprises at least three spines.

11. The system of claim 4, wherein the electrode assembly comprises at least five spines.

12. A system for atrial defibrillation in a patient comprising:
   a catheter comprising:
      an elongated catheter body having proximal and distal ends, a length of at least about 90 cm, and at least one lumen therethrough, the catheter body having one or more ring electrodes mounted at or near its distal end, and a basket-shaped electrode assembly at the distal end of the catheter body, the electrode assembly having proximal and distal ends and comprising at least three spines connected at their proximal and distal ends, each spine comprising an elongated spine electrode along its length, wherein each spine electrode has a length ranging from about 30 mm to about 80 mm, the electrode assembly having an expanded arrangement wherein the spines bow radially outwardly and a collapsed arrangement wherein the spines are arranged generally along the axis of the catheter body, the electrode assembly having a tip electrode mounted at its distal end;

an external defibrillator connected to the catheter;

an interface switch box that connects the external defibrillator to the catheter and that permits the selection of spine electrodes through which defibrillation energy is to be delivered;

an ECG recorder electrically connected to the catheter through the interface switch box; and an external pacer electrically connected to the catheter through the interface switch box.

13. A method for atrial defibrillation in a patient in need thereof comprising:

introducing into the patient a catheter comprising:
an elongated catheter body having proximal and distal ends and at least one lumen therethrough, and
a basket-shaped electrode assembly at the distal end of the catheter body, the electrode assembly having proximal and distal ends and comprising a plurality of spines connected at their proximal and distal ends, each spine comprising an elongated spine electrode along its length, the electrode assembly having an expanded arrangement wherein the spines bow radially outwardly and a collapsed arrangement wherein the spines are arranged generally along the axis of the catheter body;

introducing the electrode assembly into the heart of the patient; and applying defibrillation energy to the tissue of the heart through selected ones of the spine electrodes, leaving one or more spine electrodes through which defibrillation energy is not delivered to the heart tissue, wherein the one or more spine electrodes through which defibrillation energy is not delivered to the heart tissue are shorted together and function as a return electrode for the defibrillation energy.

14. A method for atrial defibrillation in a patient in need thereof comprising:

introducing into the patient a catheter comprising:
an elongated catheter body having proximal and distal ends and at least one lumen therethrough, and
a basket-shaped electrode assembly at the distal end of the catheter body, the electrode assembly comprising a plurality of spine electrodes and having an expanded arrangement and a collapsed arrangement;

introducing the electrode assembly into the heart of the patient; and applying defibrillation energy to tissue of the heart through selected ones of the spine electrodes, leaving one or more spine electrodes through which defibrillation energy is not delivered to the heart tissue, wherein the spine electrodes through which defibrillation energy is delivered are shorted together.

15. A method for atrial defibrillation in a patient in need thereof comprising:

introducing into the patient a catheter comprising:
an elongated catheter body having proximal and distal ends and at least one lumen therethrough, and
a basket-shaped electrode assembly at the distal end of the catheter body, the electrode assembly comprising a plurality of spine electrodes and having an expanded arrangement and a collapsed arrangement;

introducing the electrode assembly into the heart of the patient; and applying defibrillation energy to tissue of the heart through selected ones of the spine electrodes, leaving one or more spine electrodes through which defibrillation energy is not delivered to the heart tissue, wherein the one or more spine electrodes through which defibrillation energy is not delivered to the heart tissue are shorted together and function as a return electrode for the defibrillation energy.

* * * * *